United States Patent [19]

Wittrock et al.

[11] Patent Number: 4,795,510
[45] Date of Patent: Jan. 3, 1989

[54] PROCESS FOR APPLYING REINFORCING MATERIAL TO A DIAPER COVER MATERIAL

[75] Inventors: Marvin E. Wittrock, Appleton; Perry T. Handziak, Neenah, both of Wis.

[73] Assignee: Kimberly-Clark Corporation, Neenah, Wis.

[21] Appl. No.: 96,411

[22] Filed: Sep. 11, 1987

[51] Int. Cl.[4] .............................................. B31B 1/82
[52] U.S. Cl. .................... 156/64; 118/673; 156/265; 156/357; 156/519; 156/521
[58] Field of Search ................ 156/521, 522, 517–520, 156/256, 264–265, 244.24, 244.25, 244.27, 578, 356, 357; 118/673

[56] References Cited

U.S. PATENT DOCUMENTS

| | | |
|---|---|---|
| 2,289,336 | 7/1942 | Bamford . |
| 2,919,673 | 1/1960 | Williams et al. ................ 118/673 |
| 2,958,437 | 11/1960 | Mengis ................................ 216/25 |
| 3,012,481 | 12/1961 | Hughes . |
| 3,116,194 | 12/1963 | Looser ........................ 156/244.27 X |
| 3,586,586 | 6/1971 | Berg ................................ 156/519 X |
| 3,616,027 | 10/1971 | Honsel ................................ 156/265 |
| 3,850,724 | 11/1974 | Lehmacher ........................ 156/201 |
| 3,879,246 | 4/1975 | Walker ................................ 156/265 |
| 3,933,564 | 1/1976 | Jensen ................................ 156/265 |
| 4,061,527 | 12/1977 | Traise ................................ 156/519 |
| 4,357,899 | 11/1982 | Jones et al. ...................... 118/673 X |
| 4,475,969 | 10/1984 | Reed ................................ 156/152 |
| 4,642,085 | 2/1987 | Helm .................................. 493/222 |

FOREIGN PATENT DOCUMENTS

0080647 6/1983 European Pat. Off. .
2129689 5/1984 United Kingdom .

Primary Examiner—David Simmons
Attorney, Agent, or Firm—Paul Yee

[57] ABSTRACT

A technique for adhering individual patches of substrate material to spaced-apart regions of a moving web layer comprises a transporting mechanism for moving the web layer and a supplying mechanism for providing a selected substrate material. An applicating mechanism deposits a selected coating of hotmelt adhesive onto the substrate material, and a regulating mechanism automatically maintains a selected cross-directional registry between the substrate material and the deposited coating of adhesive. The coated substrate is cooled, and a directing mechanism engages the coated substrate to feed it to a separating mechanism at a selected rate. The separating mechanism segments the coated substrate into individual patches. A phasing mechanism provides a selected spatial segregation between the individual patches, and an assemblying mechanism adhesively secures the segregated patches onto selected spaced regions of the moving web layer. An indexing mechanism selectively displaces the coated substrate material from the separating mechanism when the directing mechanism is disengaged from the substrate material.

20 Claims, 5 Drawing Sheets

PROCESS FOR APPLYING REINFORCING MATERIAL TO A DIAPER COVER MATERIAL

FIELD OF THE INVENTION

This invention relates to a method and apparatus for laminating a selected substrate material to a moving web. More particularly, the present invention relates to a method and apparatus for securing separate patches of reinforcing material to a moving web of outer cover material employed to construct an absorbent article, such as a disposable diaper.

BACKGROUND OF THE INVENTION

Disposable absorbent articles, such as diapers, training pants, incontinence garments and the like, have typically employed adhesive tape tabs to secure the absorbent article about the waist of the wearer. It has been desirable to have adhesive tape tabs which are capable of being fastened and refastened several times. The refastenability of the tape tabs permits an adjustment of the fit on the wearer, and allows a selected unfastening and opening of the article for inspection. If the article is suitable for continued use, the adhesive tabs can then be refastened to again secure the garment on the wearer.

Particular disposable diaper designs have employed a film of reinforcing material secured to the outer surface of the garment cover layer to prevent tearing of the cover layer when an adhesive tape tab is peeled away. For example, U. K. Patent No. GB 2 129 689 B published 22 Oct. 1986 with the inventor listed as L. Widlund describes a disposable diaper having a thin plastic outer layer reinforced with plastic strips to allow a removal and refastening of adhesive tape fasteners. Similarly, European Patent Application No. EP 0 080 647 A1 published 8 June 1983 with the inventors listed as R. deJonckheere, et al. describes a disposable diaper having a plastic outer sheet reinforced by one or more strips to improve the tensile strength of the outer sheet in the regions where adhesive tape fasteners are applied. The reinforcing strips permit the adhesive tabs to be opened and reclosed several times without rendering the article unserviceable. The documents discussed above, however, do not disclose any method or apparatus for manufacturing the diapers with the reinforcement patch.

U.S. Pat No. 2,289,336 to A. Bamford describes a method and apparatus for applying windows of transparent material to a moving base material. The apparatus employs a rotary suction carrier which moves portions of sheet material into an applying zone at a constant rate of continuous travel. A mechanism displaces individual suction elements outwardly and substantially radially of the suction carrier to apply individual portions of sheet material to the base material.

Another technique for applying window patches to a moving web is described in U.S. Pat. No. 4,642,085 issued Feb. 10, 1987 to H. Helm. An apparatus described by Helm feeds a web of patch material to an adhesive applying mechanism. A vacuum conveyor transports the web from the adhesive applying mechanism to a severing mechanism which cuts successive window patches from a preselected length of the web in spaced relation to a portion of the web engaged on the surface of a vacuum roll. The vacuum roll then applies the patches to a moving base sheet layer.

Other techniques for applying patches to a moving web are described in U.S. Pat. No. 2,958,437 issued Nov. 1, 1960 to A. Mengis; U.S. Pat. No. 4,061,527 issued Dec. 6, 1977 to J. Traise; U.S. Pat. No. 3,933,564 issued Jan. 20, 1976 to O. Jensen; and U.S. Pat. No. 4,475,969 issued Oct. 9, 1984 to C. Reed.

In addition, various other devices have been developed to apply reinforcing strips onto selected base sheets. For example, see U.S. Pat. No. 3,616,027 issued Oct. 26, 1971 to K. Honsel; U.S. Pat. No. 3,850,724 issued Nov. 26, 1974 to H. Lehmacher; and U.S. Pat. No. 3,012,481 issued Dec. 12, 1961 to W. Hughes.

Conventional devices, such as those described above, have not been able to provide an in-line process which adequately regulates and controls the steps of applying a selected coating of adhesive onto a film substrate, separating the coated substrate into separate individual patches, and applying the patches to spaced-apart regions of a moving web layer. As a result, conventional techniques have not been adequate for tasks such as applying reinforcement patches to the outer covers of disposable absorbent garments. The techniques have generated excessive waste and have required excessive maintenance.

BRIEF DESCRIPTION OF THE INVENTION

The present invention provides a distinctive apparatus for adhering individual patches of substrate material to spaced-apart regions of a moving web layer. Generally stated, the apparatus includes transporting means for moving the web layer and supplying means for providing a selected substrate material. Applicating means deposit a selected coating of hotmelt adhesive onto the substrate material, and regulating means automatically adjust and maintain a selected cross-direction registry between the applicating means and the substrate material. Cooling means selectively reduce the temperature of the coated substrate material. Separating means segment the coated substrate material into individual patches, and directing means engage the coated substrate material to feed it into the separating means at a selected rate. Phasing means provide a selected spatial segregation between the patches, and assembling means adhesively secure the segregated patches onto selected spaced regions of the moving web layer. In a particular aspect of the apparatus of the invention, indexing means selectively displace the coated substrate material from the separating means when the directing means is disengaged from the substrate material.

The present invention further provides an improved method for adhering individual patches of substrate material to spaced-apart regions of a moving web layer. The method includes the steps of moving a selected web layer, and providing a selected substrate material. A selected coating of hotmelt adhesive is deposited onto the substrate material, and a selected cross-directional registry between the substrate material and the deposited coating of adhesive is automatically maintained. The coated substrate material is selectively cooled and engaged to feed it at a selected rate to a segmenting step. The coated substrate material is segmented into individual patches, and the patches are spatially segregated by a selected amount. The segregated patches are adhesively secured onto selected spaced-apart regions of the moving web layer. In a particular aspect of the method of the invention, the coated substrate material is selectively displaced by a selected amount when the feeding of the coated substrate is disengaged, thereby substantially preventing undesired segmenting thereof.

The distinctive method and apparatus of the invention can advantageously provide a technique which can efficiently control the securement of patches of substrate material to spaced regions of a moving web of base material during a continuous, high-speed, in-line operation. Particular embodiments of the invention can accurately control the placement of adhesive on the substrate material and can provide more complete coverage of the substrate surface without excessively contaminating machinery components. As a result, the method and apparatus of the invention can provide improved reliability, lower maintenance and reduced waste material.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The method and apparatus of the present invention are particularly suitable for adhesively securing patches of reinforcement material to the outer cover layer of an absorbent garment, such as a disposable diaper, incontinence garment, training pant or the like. It will be readily apparent, however, that the present invention can also be employed to coat adhesive onto other types of materials and to secure discontinuous segments of the material onto a predetermined web layer in a continuous in-line operation.

Figure 1:
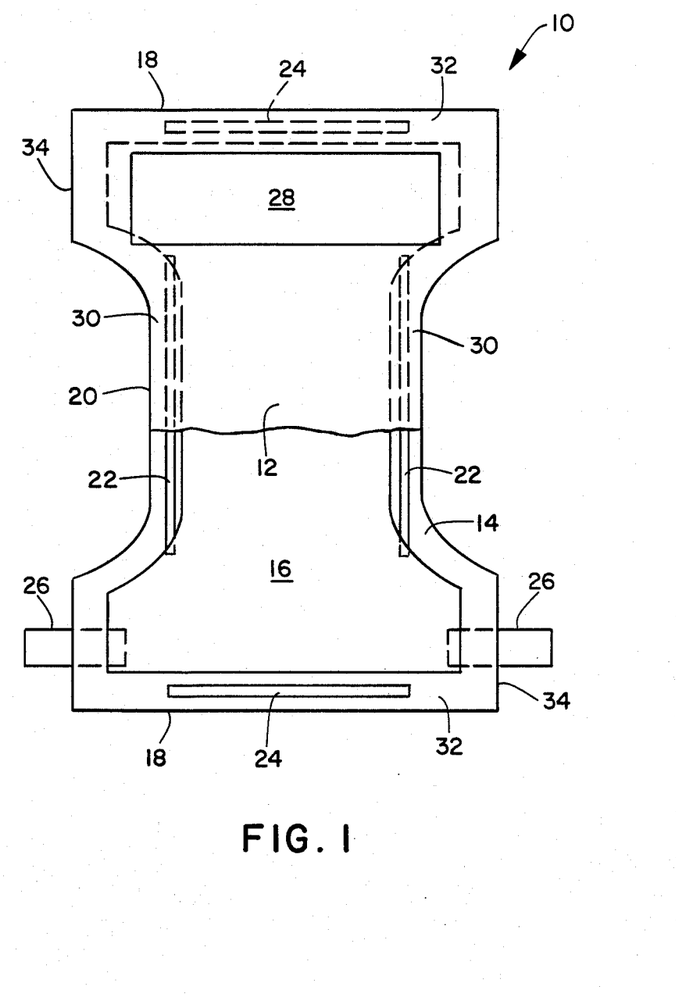
FIG. 1 representatively shows a diaper article produced with the present invention.

With reference to FIG. 1, an absorbent article, such as diaper 10, generally comprises a backsheet layer 12, a substantially liquid-permeable liner sheet layer 14, and an absorbent body 16 sandwiched between the backsheet and liner layers. Diaper 10 generally delimits front and rear waistband sections 18 which are interconnected by an intermediate section 20, and in the illustrated embodiment. The intermediate section is narrower than the waistband sections. Diaper 10 thus has a generally hourglass or I-shaped planform with the waistband sections 18 defining ear sections 34 extending oppositely along the lateral, cross-wise direction of the diaper. In the shown embodiment, backsheet 12 and liner sheet 14 are essentially coterminous and extend out past the edges of absorbent body 16 to form side margins 30 and end margins 32. The shown embodiment further includes elastic members 22 which are attached to each of the diaper side margins 30 and configured to gather and shirr the legband portions of diaper 10 to form seals or gaskets about the legs of the wearer. In addition, diaper 10 can include waist elastic members 24 secured to one or more end margins 32 to gather and shirr the waistband sections of the diaper. Two ear sections at one waistband section of the diaper, typically the rear waistband section, include securement means for fastening the diaper on the wearer. In the illustrated embodiment, the securement means comprise adhesive tape tabs 26, one end of which are factory bonded to the ears of the rear waistband of the diaper. The front waistband section of the diaper may also include a reinforcement patch 28 which strengthens the backsheet material and allows the adhesive tape tabs to be fastened and refastened against the reinforcement patch.

Typical techniques for manufacturing diapers having reinforcement patches applied thereto have ordinarily employed wound rolls of reinforcement material which have been previously coated with adhesive. As a result, the adjacent, wound layers of reinforcement material are adhesively bonded to one another and can be difficult to separate when the roll is unwound during the manufacturing process. For example, the force needed to unwind and separate the adhered layers may stretch or fracture the reinforcement material. If the strength of the adhesive is reduced, there may be insufficient bonding between the reinforcement material and the diaper backsheet. If the reinforcement material is strengthened, the cost may become excessive or the reinforcement material may acquire an undesired appearance. Other techniques for dealing with these problems have been to treat one side of the reinforcement material with a release-type coating to reduce the adhesive bond between the adjacent layers, or to interpose a separate layer of nonstick material between the adjacent layers of adhesive-coated reinforcement material. The use of the release coating, however, can unacceptably reduce the strength of the fastening bond between the adhesive tape tabs and the reinforcement material, and the use of the separate nonstick layer can be too expensive.

Because of the shortcomings encountered with pre-wound rolls of adhesive-coated reinforcing substrate material, it has been desirable to coat the adhesive onto the substrate material in-line with the manufacturing operation. Conventional in-line techniques for coating adhesive onto the substrate, however, have not been completely satisfactory. For example, the alignment and registration between the adhesive coating and the substrate layer has been inadequate. As a result, the machinery can become contaminated with excess adhesive or the substrate can have an excessively wide margin which is uncoated with adhesive. The uncoated substrate margin can then produce an undesired loose edge, which is unattached to the backsheet web material, and creates an unfinished appearance.

Figure 2:
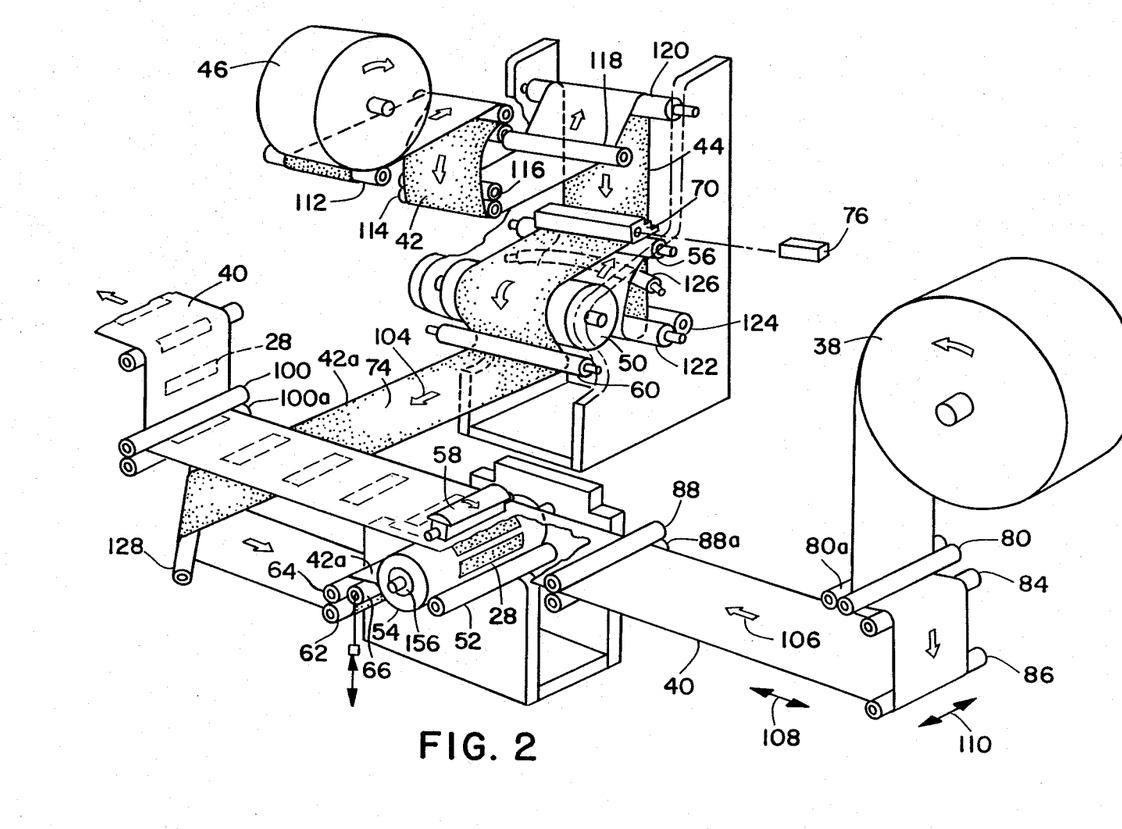
FIG. 2 representatively shows an isometric view of the apparatus of the invention wherein the coated substrate is introduced generally perpendicular to the direction of travel of the web material.

With reference to FIG. 2, the apparatus of the invention is distinctively constructed to more effectively adhere individual patches 28 of substrate material 42 to spaced-apart regions of a moving web layer 40. Transporting means, such as rollers 80, 86 and 88, move web layer 40 along a selected path 106, and supplying means, such as substrate supply roll 46, provides substrate material 42. Applicating means, such as adhesive applicator 70, deposit a selected coating of hotmelt adhesive 74 onto the layer of substrate material 42. Regulating means, such as actuator servo 76, automatically adjusts and maintains a selected cross-directional registry between applicator 70 and substrate 42. Cooling means, comprising chill roll 50, selectively reduces the temperature of the coated substrate material 42a, and separating means, comprising knife roll 52, segments the coated substrate material into individual patches 28. Directing means, such as applicator feed roll 62, engages coated substrate material 42a to feed it to knife roll 52 at a selected rate. Phasing means, such as vacuum anvil roll 54 provides a selected spatial segregation between the individual patches, and assembling means, such as stomper roll 58 adhesively secures the segregated patches onto selected spaced regions of moving web layer 40. Indexing means, such as pull-back roll 66, selectively displaces the coated substrate material from knife roll 52 when assembly feed roll 62 is disengaged from substrate material 42.

Web layer 40 is typically composed of a polymer film, such as polypropylene, polyethylene, polyester and blends thereof. Alternatively, web layer 40 may be composed of a nonwoven fibrous web, such as a spun-bonded web, a meltblown web, a bonded-carded-web or the like, composed of natural or synthetic fibers or blends thereof. For example, where web layer 40 is composed of a thin polymer film, the film thickness can be within the range of about 0.0025–0.0040 cm. Where the web layer is composed of a nonwoven fibrous web, the fibrous web can have a basis weight within the range of about 25–70 g/m$^2$.

In the shown embodiment, web material 40 is employed to construct the backsheet 12 of a diaper, and is delivered from a wound, web supply roll 38. As web layer 40 unwinds from roll 38, it passes through an unwind nip produced between counterrotating unwind rollers 80 and 80a. A dancer bar 84 maintains a selected tension on the web layer, and a guide roller 86 provides a selected positioning of the web along cross-direction 110. The cross-direction is transverse and generally perpendicular to the machine direction 108 along which web layer 40 moves. The web layer travels between counterrotating nip rollers 88 and 88a past anvil roll 54 and stomper roll 58, and then through counterrotating nip rollers 100 and 100a. After passing between nip rollers 100 and 100a, the web layer with attached reinforcement patches 28 is delivered to other apparatus which secure additional diaper components, such as the leg elastics, the absorbent pad and the liner sheet, to web layer 40.

The various rollers described herein are arranged and rotatably supported within a suitable frame, and conventional drive mechanisms (not shown) are operably connected thereto employing ordinary techniques well known to persons skilled in the art. For example, in a particular embodiment of the invention, back-up roll 56, chill roll 50, coater feed roll 60 and assembly feed roll 62 are driven from a common drive shaft employing conventional power transmission and clutch mechanisms. The technique for controlling the peripheral speeds of the individual rollers includes a precise manufacturing of the rollers to particular diameters. It is well known that the relative peripheral speeds at the surfaces of sequentially located rollers will determine the tension on that portion of the moving material located therebetween.

Substrate material 42 may be composed of a suitable polymeric film material, such as a film of polyethylene, polypropylene, polyester and the like. The film may be oriented to provide increased strength, but preferably, is an unoriented polypropylene film having a nonglossy, matte finish. In addition, the film may be printed or embossed with decorations or writings, as desired.

In the illustrated embodiment, the supplying means for providing substrate material 42 comprises a rotatable supply roll 46 and associated transport rollers. In particular, substrate 42 is threaded around a peel roller 112 which is typically held against the substrate supply roll by a suitable forcing mechanism, such as a spring (not shown). The peel roll forces the substrate material to be separated from its adjacent layer along a direction which is generally perpendicular to the surface of the substrate supply roll. This perpendicular peeling force helps to break any cohesion existing between the wound layers of substrate material. Substrate 42 is then transported around guide rollers 114 and 116 and over idler rollers 118 and 120 to a tension control means, comprising tension roller 122 and tension nip roller 124.

Tension roller 122 includes an electronic brake to exert a selected tensioning drag onto the moving substrate material 42. The tension nip roll is constructed and arranged to maintain an operable engagement between moving substrate 42 and tension roller 122.

Substrate 42 is then directed over an arcuate, spreader roll 126 which helps to eliminate creases and wrinkles in the moving substrate. The spreader roll is curved along its longitudinal axial dimension, and moving substrate 42 is arranged to contact the spreader roll along the convexly-bowed area of the roller. Suitable spreader rollers are available from Mount Hope, a division of SW Paper Group located in Tauton, Mass.

Substrate 42 then moves over back-up roller 56, which is located adjacent to applicator 70 and supports the substrate during the process of depositing a selected pattern of adhesive thereon. In the shown embodiment, back-up roller 56 is a driven roll which delivers substrate material 42 past adhesive applicator 70 at a selected, predetermined speed.

Applicator 70 deposits a suitable coating of hotmelt adhesive onto the adjacent surface of substrate 42 in a selected pattern and at a selected add-on amount. In the illustrated embodiment, for example, applicator 70 extrudes a substantially continuous adhesive layer having a generally uniform thickness over the surface of moving substrate 42.

Various hotmelt adhesives can be employed with the present invention. Suitable hotmelt adhesives include, for example, National Starch 70-2811 distributed by National Starch and Chemical Corporation located in Bridgewater, N.J.

The coated substrate then moves past a cooling means, comprising chill roller 50, and past coater feed roll 60. In the illustrated embodiment, chill roller 50 and coater feed roll 60 are driven rolls which are suitably constructed and arranged to maintain selected tensions on substrate 42. In particular, chill roll 50 is rotated at a selected speed by a suitable drive mechanism (not shown) which establishes a predetermined tension in the portion of substrate 42 located between chill roll 50 and back-up roll 56. The predetermined tension should be adjusted to maintain a substantially flat contact between back-up roll 56 and substrate 42 along the cross-direction, but should be kept low enough to prevent excessive stretching of the substrate when it becomes heated by contact with the hotmelt adhesive from applicator 70.

After the coated substrate has been suitably cooled by chill roller 50, the coated surface of the substrate is engaged by coater feed roll 60 to advance it along substrate path 104. The engagement against the coated surface can advantageously reduce slippage and improve the control of the substrate movement. To ensure a reliable separation of the substrate from feed roll 60, however, the feed roll should include a suitable release coating, such as that provided by silicone rubber. In the shown embodiment, substrate path 104 is positioned generally perpendicular to web path 106. As a result, a substrate turn bar 128 is employed to reposition the substrate path along a direction which is generally parallel with web path 106. The coated substrate is then engaged by an assembly feed roll 62 and its associated nip roll 64. Assembly feed roller 62 directs the coated substrate to a separating means comprising vacuum anvil roller 54 and knife roller 52. The assembly feed roller is driven at a suitable speed to move coated substrate 42 to anvil roller 54 at a rate which produces a desired patch size.

Anvil roller 54 is rotated by a suitable drive mechanism (not shown) to produce a speed at its peripheral surface which substantially matches the speed of web layer 40. Typically, the peripheral speed of anvil roller 54 is greater than the speed at which assembly feed roller 62 introduces coated web substrate 42. As a result, a portion of the coated substrate is positioned in slipping engagement with the surface of anvil roller 54, and the slipping engagement is maintained by a vacuum force provided within the anvil roller.

Knife roller 52 includes a cutting blade which engages and separates a patch 28 of coated substrate material during each revolution of the knife roller. The speed of knife roller 52 is suitably coordinated with the speed of web layer 40 such that one reinforcement patch 28 is produced for each machine-direction length of web layer 40 that corresponds to a single diaper article. In addition, the rotational speed of assembly feed roller 62 is coordinated with the rotational speed of knife roller 52 such that the desired amount of coated substrate material is delivered onto vacuum anvil roller 54 during the time period spanned by one revolution of the knife roller. Once knife roller 52 engages and segments coated substrate 42 into individual patches 28, the vacuum anvil roller forcibly engages the separated patch and accelerates it to provide a selected phasing and spatial segregation between the individual patches. In addition, the acceleration of the segregated patches substantially matches the speed of the patch to the speed of web layer 40 to allow an accurate adhesive assembly between the patch and the moving web layer. To further enhance the adhesion between the patch and the web layer, a rotatable stomper roll 58 periodically engages the laminated arrangement of web 40 and patch 28 to provide a pressuring force which enhances the adhesion between the individual patches and the moving web layer. Once the patches 28 are secured to web layer 40, the assembly is transported for further assembly of other diaper components.

The reliability of the apparatus of the invention can be advantageously enhanced by the incorporation of pull-back roller 66. The pull-back roller is constructed and arranged for selective indexing along an operating path which produces an effective engagement between the pull-back roller and substrate 42. In particular, pull-back roller 66 is displaced against coated substrate 42 at such time that assembly feed roller is removed from driving engagement with the coated substrate. This operation draws the substrate material away from anvil roll 54 and retracts substrate 42 away from the point of engagement between the anvil roll and knife roller 52. The operation ensures a reliable spatial separation between the substrate material and the rotary knife 52, and prevents the undesired cutting of slivers of coated substrate material whenever the power drive to assembly feed roll 62 is disengaged to allow machine maintenance. The presence of slivers of substrate material can clog the machine and necessitate excessive maintenance.

As discussed above, tension roller 122 provides the required tension control of the polypropylene substrate during the coating process. In the shown embodiment, the tension roller comprises a silicone-rubber covered steel tube mounted on a bearing-supported shaft by means of tapered bushings. An electric brake is mounted to the end of the shaft. The rubber covering prevents the substrate from slipping on the tension roller surface and causes the roll to rotate as the substrate is pulled therefrom. For example, where substrate 42 is composed of unoriented polypropylene, the rubber coating has a durometer value between about 40–45, Shore A. The tension on substrate 42 is controlled by applying voltage to the electric brake which restricts the rotation of the roll. The tension force experienced by the substrate as it is pulled from tension roller 122 is proportional to the applied brake voltage. Suitable electric brakes are available from Magpower, a company located at Fenton, Mass.

Tension nip roller 124 provides the normal force between substrate 42 and tension roller 122 needed to prevent slippage between the substrate and the peripheral surface of tension roller 122. The tension nip roller is coated with a material known as "Endura 203" to provide suitable release characteristics. This material is distributed by Engineered Devices, Inc. located in Royal Oak, Mich. A suitable support mechanism, such as a pivot bracket and air cylinders can be employed to establish the required pressuring engagement between tension roller 122 and tension nip roller 124.

Back-up roller 56 supports the substrate material to provide dimensional stability between the substrate and applicator 70 to produce a substantially smooth, even adhesive coating onto substrate 42. In the shown embodiment, back-up roller 56 comprises a thin-walled steel tube mounted to a driven, bearing-supported shaft by means of welded end caps. The back-up roller is coated with about 55 durometer silicone rubber to provide suitable release characteristics and to provide a cushioned surface for the operation of applicator 70. The rubber also provides a resilient roll surface which compensates for roll runout and allows foreign matter to pass between back-up roller 56 and applicator 70.

Chill roll 50 cools coated substrate 42 to room temperature to prevent it from bonding to coater feed roller 60 and causing a wrap-up. In the illustrated embodiment, chill roll 50 comprises a chambered steel roll through which cooling water passes. The cooling water is supplied by means of a mixing valve from a commercial cooling unit, such as a refrigeration unit available from Filtrene Co. located in Harrisville, New Hampshire. Chill roller 50 includes a chrome peripheral surface which is impregnated with PTFE (polytetrafluoroethylene) to provide a suitable nonstick surface. The chill roll is mechanically driven off a clutch drive mechanism and the chill roll temperature is maintained at approximately 68° F.

Assembly feed roller 62 supplies coated substrate 42 to knife roller 52 and anvil roll 54 at the rate needed to produce a given machine-direction, patch length. The assembly feed roller comprises a steel tube mounted to a bearing-supported, driven shaft by means of taperlock bushings. The assembly feed roller is also covered with an appropriate silicone rubber to provide a nonslip surface with suitable release characteristics.

Pull-back roller 66 retracts the coated substrate away from the strike point between knife roller 52 and vacuum anvil roll 54 at such times that the assembly feed roller 62 is stopped and anvil roller 54 is still turning. This prevents the knife roller from cutting slivers off the leading edge of substrate 42 and causing a build-up of material on the knife and anvil rollers. In the shown embodiment, pull-back roller 66 comprises a rubber-coated steel tube mounted on a dead shaft by means of roller bearings. The dead shaft is supported on each end by air cylinders which lift the pull-back roller when the clutch for the assembly feed roller 64 is disengaged. As the pull-back roller rises, it contacts and lifts substrate 42a to draw it away from the knife strike point, thereby eliminating the possibility of the knife striking the leading edge of substrate 42. The air cylinders are also constructed and arranged to lower pull-back roller 66 away from engagement with substrate 42 at such time that the assembly feed roller clutch is reengaged.

Figure 4:
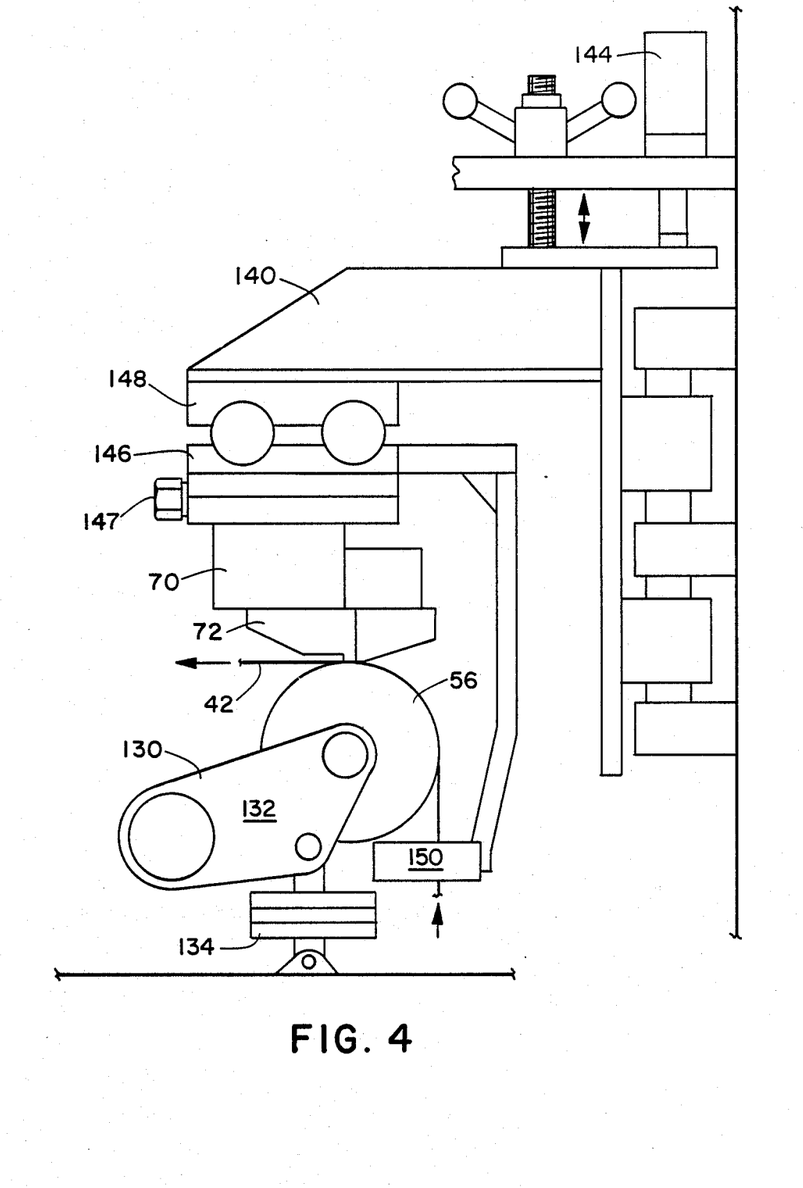
FIG. 4 representatively shows a schematic side elevational view of the coating nozzle and associated position regulating components.

With reference to FIG. 4, back-up roller 56 is carried and supported by a back-up roll bracket 130 which holds back-up roll 56 firmly in position during the coating operation and lowers the back-up roll when the machine is not operating. In the illustrated embodiment, back-up roller 56 is capable of being lowered approximately one-half inch to separate substate 42 from applicator 70 and prevent hotmelt adhesive from burning through the substrate. The back-up roller is automatically raised back into position when the coating operation is started. The shown embodiment of bracket 130 comprises two pivotable arms, which, for example, may rotate about the axis of chill roll 50 and carry the back-up roller shaft mounted on their opposite ends. A back-up roll actuator is employed to selectively move the back-up roll into adjacent relation with the applicator nozzle. For example, in the shown embodiment, back-up roller 56 is raised or lowered by energizing or deenergizing two air cylinders 134 which rotate bracket arms 132 about their common axis. The air cylinders may, for example, comprise two and one-half inch bore cylinders energized with about 80 psi air to produce an upward force of about 393 pounds at each bracket arm. This large force is capable of preventing excessive vibration of back-up roller 56 during the coating operation. In a preferred embodiment of the invention, the apparatus is configured such that the back-up roll air cylinders 134 are allowed to bottom out when the cylinders are energized. With such a configuration, a separate adjustable stop is not required to control and limit the operable stroke of the air cylinders. Such stops can be forced out of adjustment by the impacts experienced during repeated actuations of the air cylinders, and can require excessive maintenance.

The applicating means for depositing hotmelt adhesive onto substrate 42 may be configured to deposit a regular or irregular pattern of adhesive to provide a continuous or discontinuous coating, as desired. In a particular embodiment of the invention, adhesive applicator 70 is configured to extrude a substantially uniform, continuous coating of hotmelt adhesive over substantially the entire area of the adjacently located surface of substrate 42. The amount of adhesive add-on is approximately 25 g/m$^2$ and forms a coating of adhesive having a thickness within the range of about 0.002–0.003 cm.

With reference to FIG. 4, applicator 70 includes an extruder head support 140 which holds and maintains a wide band, slot extrusion nozzle 72 in a substantially fixed position during the coating operation. The extruder head support also provides a vertical adjustment mechanism, such as a screw adjustment, for setting the coating gap between nozzle 72 and back-up roller 56. The illustrated embodiment of the invention is, for example, configured to provide an extrusion gap of about 0.002 inches (about 0.005 cm). Head support 140 can further include a support actuator, such as maintenance air cylinder 144, which selectively raises the head support along with extrusion nozzle 72 away from back-up roller 56 to improve accessibility during maintenance.

The illustrated embodiment of the invention includes a machine direction slide block 146 employed to position the center of nozzle 72 forward or backward with respect to the top dead center of back-up roller 56. Typically, the center of nozzle 72 is placed approximately three-sixteenth of an inch upstream from the top dead center of back-up roll of 56, as measured in a direction counter to the movement of substrate 42. With the illustrated embodiment, position adjustments along the machine direction can be made by loosening anchor bolts, which hold the slide block, and turning adjustment screw 147 to move the position of nozzle 72 upstream or downstream relative to the movement of substrate 42, as desired.

A further aspect of the invention, includes a distinctive regulating means for automatically adjusting and maintaining a selected cross-directional registry between applicator 70 and moving substrate 42. In particular, the invention can include a mechanism for automatically traversing applicator 70 along cross-direction 110 to maintain a predetermined registry between applicator nozzle 72 and substrate 42. In the embodiment illustrated in FIGS. 4 and 5, the regulating means comprises cross-direction slide block 148, edge sensors 150, signal processor 152, and cross-direction guide actuator 154.

Figure 5:
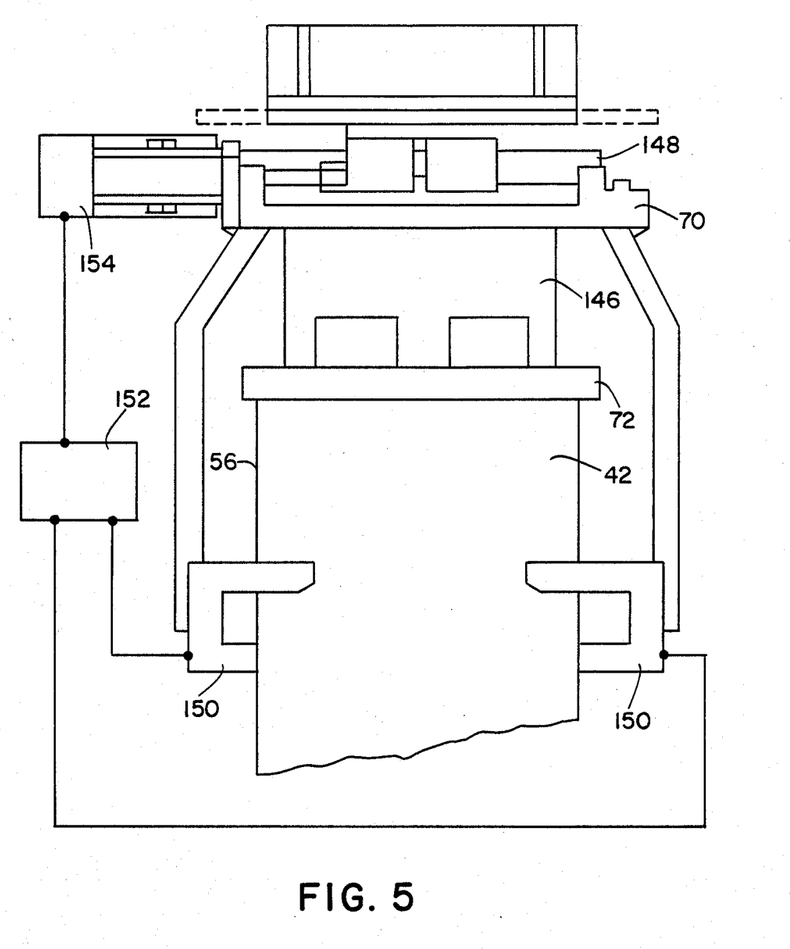
FIG. 5 representatively shows a schematic end view of the coating nozzle and associated position regulating equipment.

Cross-direction slide block 148 is employed to center applicator nozzle 72 relative to the cross-direction of substrate 42, and a guide actuation system is employed to automatically maneuver the cross-direction slide block and nozzle 72 to substantially follow the centerline of substrate 42. Electronic edge sensors 150, such as photoelectric detectors, are located at each side edge 44 of substrate 42 to detect the position of the substrate and provide output signals to processer 152. Processer 152 analyzes the sensor information and sends an appropriate signal to guide actuator 154 to adjust the cross-directional position of nozzle 72. A suitable mechanism for controlling the position of nozzle 72 is a modified electomechanical guiding system distributed by Fife Corporation located in Oklahoma City, Okla. The FIFE mechanism is ordinarily employed to engage a moving web with a web guide component to adjust the web position relative to the axial dimension of a guide roller. For the purposes of the present invention, however, the FIFE guide is distinctively modified by reversing the logic within the signal processor and by reconfiguring the actuator mechanism to move slide block 148 instead of a web guide. As a result, guide actuator 154 can operably traverse the adhesive applicator along the cross-direction of substrate 42 in response to the signals generated by edge sensors 150.

The technique of the present invention, which selectively moves the position of applicator 70 during the coating operation, can advantageously provide a more accurate and precise positioning of adhesive on substrate 42. The system has a lower response time which reduces the possibility of depositing adhesive past the side edge of substrate 42 and onto back-up roller 56. As a result, the method and apparatus of the present invention can more accurately deposit adhesive over substantially the entire surface of substrate 42 leaving only a very narrow margin of substrate material which is uncoated with adhesive. The uncoated margin at each edge of substrate 42 has a cross-directional width of less than about 0.6 cm, and preferably has a cross-directional width of less than about 0.3 cm.

The substrate assembler section of the present invention is configured to cut, separate and assemble adhesive coated substrate patches to the diaper outer cover material comprising web layer 40. In particular, coated substrate 42 is fed onto vacuum anvil roll 54 at a rate which is less than the peripheral surface speed of the anvil roll, thereby causing the anvil roll surface to slip beneath the substrate material. The anvil roll rotates one-half revolution per diaper. That is, the anvil roll rotates one-half revolution during the time period in which a length of web 40 corresponding to one diaper moves past the anvil roll. Knife roll 52 rotates at one revolution per diaper and interferes with the anvil roll to sever substrate 42 between the knife and anvil. The cut portion of substrate 42 corresponds to reinforcement patch 28 and is quickly accelerated to match the surface speed of anvil roll 54, against which the patch is held flat during the assembly operation. The anvil roll thus holds the coated substrate 42 flat during the cutting operation, and separates the cut substrate patches 28 from the uncut substrate so that the patch can be suitably laminated to the diaper cover material comprising web layer 40.

In the shown embodiment, vacuum anvil roll 54 comprises an outer steel shell with welded end caps supported on a shaft. Approximately 60 vacuum cross-holes are drilled parallel to the roll axis and spaced every 6° around the circumference of the roll. Eleven, equally spaced, radially extending holes are then drilled into each cross-hole from the outer surface of the anvil roll. The anvil roll holds two carbide anvil inserts which are positioned 180° apart around the roll circumference. In a preferred embodiment of the invention, the anvil roll is coated with Cermetco No. 8D, a product manufactured by CSI Corporation located in Butler, Wisconsin. This coating provides suitable release and wear characteristics.

Conventional vacuum manifolds 156 are located on each axial end of the anvil roll in a manner well known in the art to provide a suitable vacuum. Each vacuum manifold is configured in a conventional manner to provide a vacuum force around approximately 270° of the anvil roll circumference. In the shown embodiment, the manifolds are arranged to provide a slip vacuum area and a separate transfer vacuum area. The slip vacuum area is located along a surface region of vacuum roll 54 which is generally adjacent to and preceding knife roll 52, and the transfer vacuum area is located along a surface region of vacuum roll 54 which is generally intermediate the knife roll and stomper roll 58. In a preferred aspect of the invention, the slip vacuum force is lower than the transfer vacuum force. In particular, the slip vacuum level should be set just high enough to hold the coated substrate flat on the anvil roll surface, allowing the roll to slip freely beneath the substrate without grabbing it. Typically, the slip vacuum level is set at about 8 inches of water. The transfer vacuum is set at a higher level of about 20 inches of water to ensure that patch 28 remains on the anvil roll surface until it is transferred to web 40. Blow-off ports are provided on each vacuum manifold to ensure that untransferred substrate patches are reliably removed from the anvil roll and directed away from the apparatus.

Knife roll 52 in the shown embodiment is a driven roll and is provided with a centric clutch to provide overload protection. In addition, a conventional oil-wipe mechanism is employed to provide a substantially uniform lubrication of the knife blade. A suitable lubricant is propylene glycol which is transferred to the knife blade employing a rotatable felt-wipe mechanism.

Figure 3:
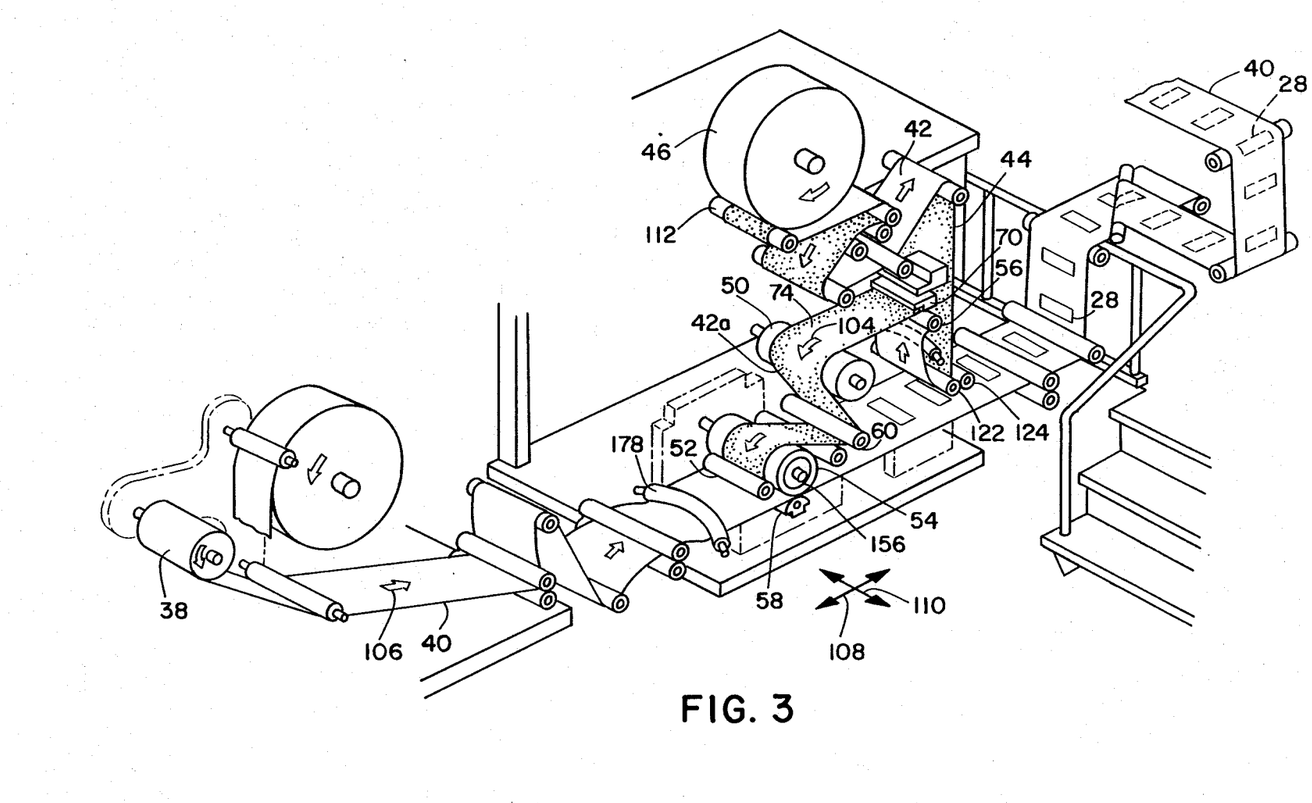
FIG. 3 representatively shows an isometric view of an embodiment of the invention wherein the coated substrate is introduced generally parallel to the direction of travel of the web material.

With reference to FIG. 3, an alternative embodiment of the invention may be constructed and arranged to introduce coated substrate 42 along a direction which is generally parallel to the direction of travel of web layer 40. The specific arrangement of the components differs somewhat from the embodiment representatively shown in FIG. 2. In particular, a spreader bar 178 is employed to prevent wrinkles in web layer 40 prior to the assembly of patches 28 thereto. In addition, coater feed roll 60 perform the dual function of drawing coated substrate 42 from chill roll 50 and of feeding the coated substrate to anvil roll 54 and knife roll 52. The arrangement is relatively simpler than the embodiment shown in FIG. 2, since assembly feed roll 62 may be eliminated.

Having thus described the invention in rather full detail, it will be readily apparent that various changes and modifications may be made without departing from the spirit of the invention. All of such changes and modifications are contemplated as being within the scope of the invention, as defined by the subjoined claims.

We claim:

1. A method for adhering individual patches of substrate material to spaced-apart regions of a moving web layer, comprising the steps of:
   a. moving a selected web layer;
   b. providing a selected substrate material;
   c. depositing a selected coating of hotmelt adhesive onto said substrate material;
   d. automatically maintaining a selected cross-directional registry between said substrate material and said deposited coating of adhesive;
   e. selectively cooling said coated substrate material;
   f. engaging said coated substrate material to feed it at a selected rate to a segmenting step;
   g. segmenting said coated substrate material into individual patches;
   h. spatially segregating said patches by a selected amount,
   i adhesively securing said segregated patches onto selected spaced-apart regions of said moving web layer; and
   j. selectively retracting said coated substrate material by a selected amount to draw said coat substrate material away from a striking point of said segmenting step when said feeding of the coated substrate material is disengaged and stopped, thereby substantially preventing undesired segmenting of said coated substrate material.

2. A method as recited in claim 14, wherein said automatic maintaining step (d) comprises the steps of:
   detecting side edges of said substrate material with sensors;
   traversing said step (c) of depositing material along a cross-direction of the substrate material in response to signals generated by said sensors.

3. A method as recited in claim 1, wherein said segmenting step (g) segments said coated substrate material into individual patches with a separating means; and wherein said retracting step (j) provides a spatial separation between said coated substrate material and a striking point of said separating means.

4. A method as recited in claim 1, wherein said maintaining step (d) comprises the steps of:
   detecting the position of said substrate with electronic sensors located at each side edge of said substrate, and providing sensor output signals;
   analyzing said sensor output signals with a signal processor to send a signal to a guide actuator; and
   traversing a cross-directional positioning of said depositing step (c) to substantially follow a centerline of said substrate.

5. A method as recited in claim 4, wherein said maintaining step (d) produces side margins of said substrate which are uncoated with said adhesive and measure not more than about 0.6 cm in cross-directional width.

6. A method as recited in claim 4, wherein said maintaining step (d) produces side margins of said substrate which are uncoated with said adhesive and measure not more than about 0.3 cm in cross-directional width.

7. An apparatus for adhering individual patches of substrate material to spaced-apart regions of a moving web layer, comprising:
   a. transporting means for moving the web layer;
   b. supplying means for providing a selected substrate material;
   c. applicating means for depositing a selected coating of adhesive onto said substrate material;
   d. regulating means for automatically traversing said applicating means to maintain a selected cross-directional registry between said applicating means and substrate material;
   e. cooling means for selectively reducing the temperature of said coated substrate material;
   f. separating means for segmenting said coated substrate material into individual patches;
   g. directing means for feeding said coated substrate material to said separating means at a selected rate;
   h. phasing means for providing a selected spatial segregation between said individual patches;
   i. assembling means for adhesively securing said segregated patches onto selected spaced regions of said moving web layer; and
   j. indexing means for selectively retracting said coated substrate to draw said coated substrate away from said separating means and provide a spatial separation between said coated substrate and a strike point of said separating means when said directing means is stopped.

8. An apparatus as recited in claim 7, wherein said regulating means maintains said cross-directional registry between the applicating means and substrate material to thereby produce side margins of said substrate material which are uncoated with said adhesive and measure not more than about 0.3 cm in crossdirectional width.

9. An apparatus as recited in claim 7, wherein said applicating means comprises:
   an applicator nozzle for depositing said adhesive onto said substrate material;
   a back-up roll positioned adjacent to said applicator nozzle for supporting said substrate material during the depositing of adhesive thereon; and
   a back-up roll actuator for selectively moving said back-up roll into adjacent relation with waid applicator nozzle, wherein said back-up roll actuator includes an air cylinder for lowering said back-up roll when said apparatus is not operating and for automatically raising said back-up roll when said depositing of adhesive is started, and wherein said air cylinder is arranged to bottom out when said air cylinder is energized.

10. An apparatus as recited in claim 7, wherein said regulating means comprises electronic sensors located at each side edge of said substrate to detect the position of said substrate and provide sensor output signals; and a signal processor for analyzing said sensor output signals and for sending a signal to a guide actuator to traverse a cross-directional positioning of said applicating means to substantially follow a centerline of said substrate.

11. An apparatus as recited in claim 7, wherein said regulating means maintains said cross-directional registry between the applicating means and substrate material to thereby produce side margins of said substrate material which are uncoated with said adhesive and measure not more than about 0.6 cm in cross-directional width.

12. An apparatus as recited in claim 8, wherein said regulating means maintains said cross-directional registry between the applicating means and substrate material to thereby produce side margins of said substrate material which are uncoated with said adhesive and measure not more than about 0.6 cm in cross-directional width.

13. An apparatus as recited in claim 8, further comprising a support actuator for selectively moving said nozzle away from said back-up roll.

14. An apparatus for adhering individual patches of substrate material to spaced-apart regions of a moving web layer, comprising:
   a. transporting means for moving the web layer;
   b. supplying means for providing a selected substrate material;
   c. applicating means for depositing a selected coating of hotmelt adhesive onto said substrate material;
   d. regulating means for automatically adjusting and maintaining a selected cross-directional registry between said applicating means and said substrate material;
   e. cooling means for selectively reducing the temperature of said coating substrate material;
   f. separating means for segmenting said coating substrate material into individual patches;
   g. directing means for engaging said coated substrate material to feed it to said separating means at a selected rate;
   h. phasing means for providing a selected spatial segregation between said individual patches; and
   i. assembling means for adhesively securing and transferring said segregated patches onto selected spaced regions of said moving web layer;

j. wherein said assembling means includes a stomper roll; said phasing means includes a vacuum roll having a vacuum manifold; and wherein said vacuum roll and vacuum manifold are arranged to provide a slip vacuum surface area generally adjacent to and preceding said separating means, provide a transfer vacuum surface area generally intermediate said separating means and said stomper roll, provide a vacuum force at said slip vacuum are which is less than a vacuum force provided at said transfer vacuum area, and provide blow-off ports to remove untransferred patches from said vacuum roll.

15. An apparatus as recited in claim 14, wherein said applicating means comprises:

an applicator nozzle for depositing said adhesive onto said substrate material;
   a back-up roll positioned adjacent to said applicator nozzle for supporting said substrate material during the depositing of adhesive thereon; and
   a back-up roll actuator for selectively moving said back-up roll into adjacent relation with said applicator nozzle, wherein said back-up roll actuator includes an air cylinder for lowering said back-up roll when said apparatus is not operating and for automatically raising said back-up roll when said depositing of adhesive is started, and wherein said air cylinder is arranged to bottom out when said air cylinder is energized.

16. An apparatus as recited in claim 14, further comprising indexing means for selectively retracting said coated substrate away from engagement with a striking point of said separating means when said directing means is stopped.

17. An apparatus as recited in claim 14, wherein said regulating means maintains said cross-directional registry between the applicating means and substrate material to thereby produce side margines of said substrate material which are uncoated with said adhesive and measure not more than about 0.3 cm in cross-directional width.

18. An apparatus as recited in claim 14, wherein said regulating means comprises electronic sensors located at each side edge of said substrate to detect the position of said substrate and provide sensor output signals; and a signal processor for analyzing said sensor output signals and for sending a signal to a guide actuator to traverse a cross-directional positioning of said applicating means to substantially follow a centerline of said substrate.

19. An apparatus for adhering individual patches of substrate material to spaced-apart regions of a moving web layer, comprising:

a. transporting means for moving the web layer;
   b. supplying means for providing a selected substrate material;
   c. applicating means for depositing a selected coating of adhesive onto said substrate material;
   d. regulating means for automatically traversing said applicating means to maintain a selected cross-directional registry between said applicating means and substrate material, wherein said regulating means inlcudes electronic sensors located at each side edge of said substrate to detect the position of said substrate and provide sensor output signals, and a signal processor for analyzing said sensor output signals and for sending a signal to a guide actuator to adjust a cross-directional positioning of said applicating means to substantially follow a centerline of said substrate, and wherein said regulating means is arranged to produce side margins of said substrate material which are uncoated with said adhesive and measure not more than about 0.6 cm in cross-directional width;
   e. cooling means for selectively reducing the temperature of said coated substrate material;
   f. separating means for segmenting said coated substrate material into individual patches;
   g. directing means for engaging said coated substrate material to feed it to said separating means at selected rate;
   h. phasing means for providing a selected spatial segregation between said individual patches; and
   i. assembling means for adhesively securing said segregated patches onto selected spaced regions of said moving web layer.

20. An apparatus as recited in claim 19, wherein said regulating means is arranged to produce side margins of said substrate material which are uncoated with said adhesive and measure not more than about 0.3 cm in cross-directional width.

* * * * *

UNITED STATES PATENT AND TRADEMARK OFFICE
CERTIFICATE OF CORRECTION

PATENT NO. : 4,795,510
DATED : January 3, 1989
INVENTOR(S) : Marvin E. Wittrock, Perry T. Handziak It is certified that error appears in the above-identified patent and that said Letters Patent is hereby corrected as shown below:

IN THE SPECIFICATIONS:

Column 12, line 30, delete "perform" and substitute therefor -- performs --.

IN THE CLAIMS:

Column 14, line 11, delete "waid" and substitute therefor -- said --.

Column 14, line 59, delete "coating" and substitute therefor -- coated --.

Column 15, line 10, delete "are" and substitute therefor -- area --.

Column 15, line 38, delete "margines" and substitute therefor -- margins --.

Column 16, line 17, delete "inlcudes" and substitute therefor -- includes --

Signed and Sealed this

Twenty-first Day of November, 1989

Attest:

JEFFREY M. SAMUELS

*Attesting Officer*        *Acting Commissioner of Patents and Trademarks*